US00PP32425P2

(12) United States Plant Patent
Steffen

(10) Patent No.: US PP32,425 P2
(45) Date of Patent: Nov. 3, 2020

(54) ***ISOTOMA* PLANT NAMED 'ISOPAPI'**

(50) Latin Name: *Isotoma axillaris*
Varietal Denomination: Isopapi

(71) Applicant: Elke Steffen, Erfurt (DE)

(72) Inventor: Elke Steffen, Erfurt (DE)

(73) Assignee: Elsner pac Jungpflanzen GbR, Thiendorf (DE)

( * ) Notice: Subject to any disclaimer, the term of this patent is extended or adjusted under 35 U.S.C. 154(b) by 0 days.

(21) Appl. No.: 16/602,799

(22) Filed: Dec. 3, 2019

(51) Int. Cl.
*A01H 5/02* (2018.01)
*A01H 6/26* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Isotoma* plant named 'Isopapi' characterized by its broadly upright plant habit; moderately vigorous growth habit; freely branching habit; freely flowering habit; purple violet-colored flowers; and good garden performance with plants flowering throughout the summer into the autumn.

2 Drawing Sheets

Figure 1:
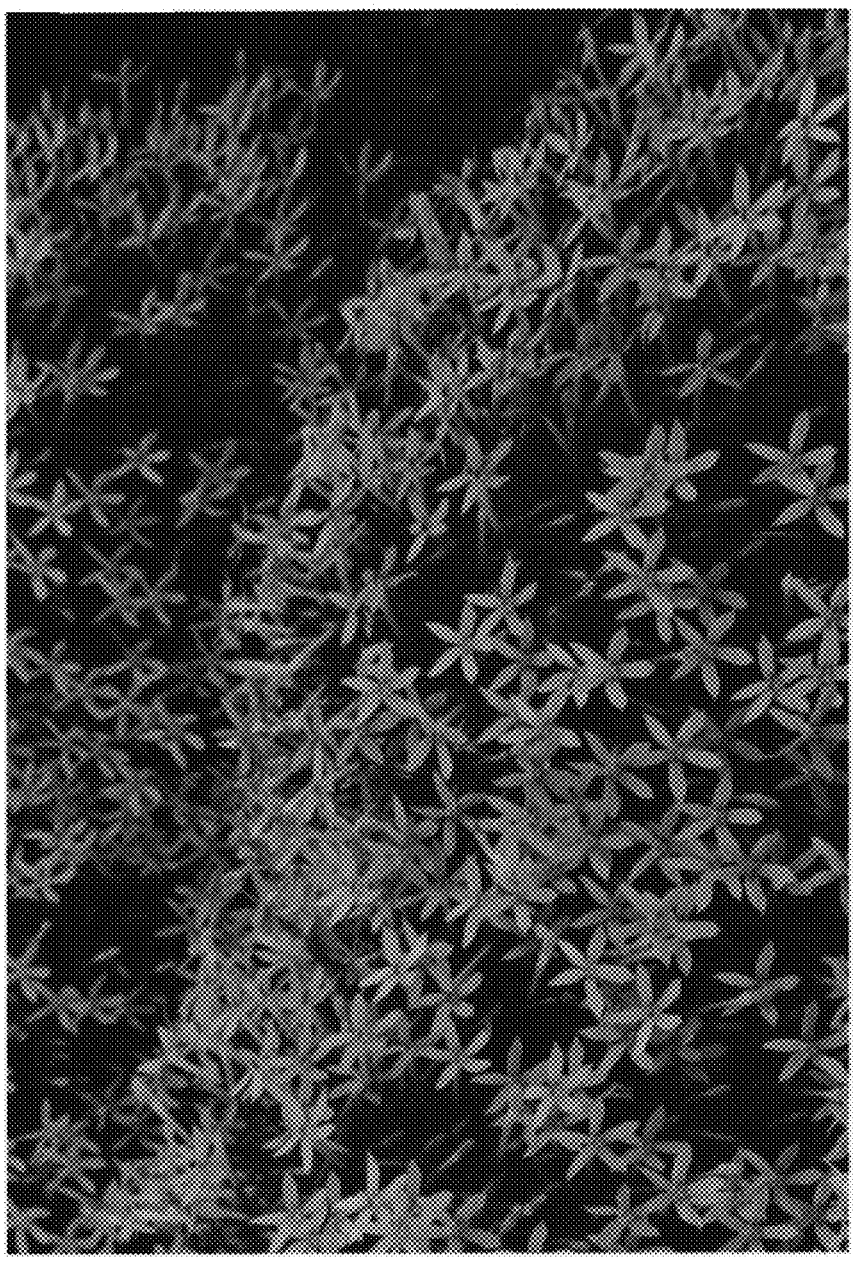

Botanical designation: *Isotoma axillaris*.
Cultivar denomination: 'ISOPAPI'.

BACKGROUND OF THE INVENTION

The present invention relates to a new and distinct cultivar of *Isotoma* plant, botanically known as *Isotoma axillaris*, commonly referred to as Rock Isotome and hereinafter referred to by the name 'Isopapi'.

The new *Isotoma* plant is a product of a planned breeding program conducted by the Inventor in Dresden, Germany. The objective of the breeding program is to create new freely-flowering *Isotoma* plants with attractive flower coloration and long flowering period.

The new *Isotoma* plant originated from a cross-pollination made by the Inventor during the summer of 2012 in Dresden, Germany of two unnamed proprietary selections of *Isotoma axillaris*, not patented. The new *Isotoma* plant was discovered and selected by the Inventor as a single flowering plant within the progeny of the stated cross-pollination in a controlled greenhouse environment in Dresden, Germany during the summer of 2013.

Asexual reproduction of the new *Isotoma* plant by vegetative terminal cuttings in a controlled greenhouse environment in Dresden, Germany since the summer of 2013 has shown that the unique features of this new *Isotoma* plant are stable and reproduced true to type in successive generations.

SUMMARY OF THE INVENTION

Plants of the new *Isotoma* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Isopapi'.

These characteristics in combination distinguish 'Isopapi' as a new and distinct *Isotoma* plant:

1. Broadly upright plant habit.
2. Moderately vigorous growth habit.
3. Freely branching habit.
4. Freely flowering habit.
5. Purple violet-colored flowers.
6. Good garden performance with plants flowering throughout the summer into the autumn.

Plants of the new *Isotoma* differ from plants of the parent selections primarily in plant and flowering habit as plants of the new *Isotoma* are more freely branching and freely flowering than plants of the parent selections.

Plants of the new *Isotoma* can be compared to plants of *Isotoma axillaris* 'Beth's Blue', not patented. In side-by-side comparisons, plants of the new *Isotoma* and 'Beth's Blue' differ primarily in the following characteristics:

1. Plants of the new *Isotoma* are slightly taller than plants of 'Beth's Blue'.
2. Plants of the new *Isotoma* flower one to two weeks earlier than plants of 'Beth's Blue'.
3. Plants of the new *Isotoma* and 'Beth's Blue' differ in flower color as plants of the new *Isotoma* have purple violet-colored flowers whereas plants of 'Beth's Blue' have violet blue-colored.

BRIEF DESCRIPTION OF THE PHOTOGRAPHS

The accompanying colored photographs illustrate the overall appearance of the new *Isotoma* plant showing the colors as true as it is reasonably possible to obtain in colored reproductions of this type. Colors in the photographs may differ slightly from the color values cited in the detailed botanical description which accurately describe the colors of the new *Isotoma* plant.

The photograph on the first sheet (FIG. 1 of 2) is a side perspective view of typical flowering plants of 'Isopapi' grown in an outdoor nursery.

Figure 2:
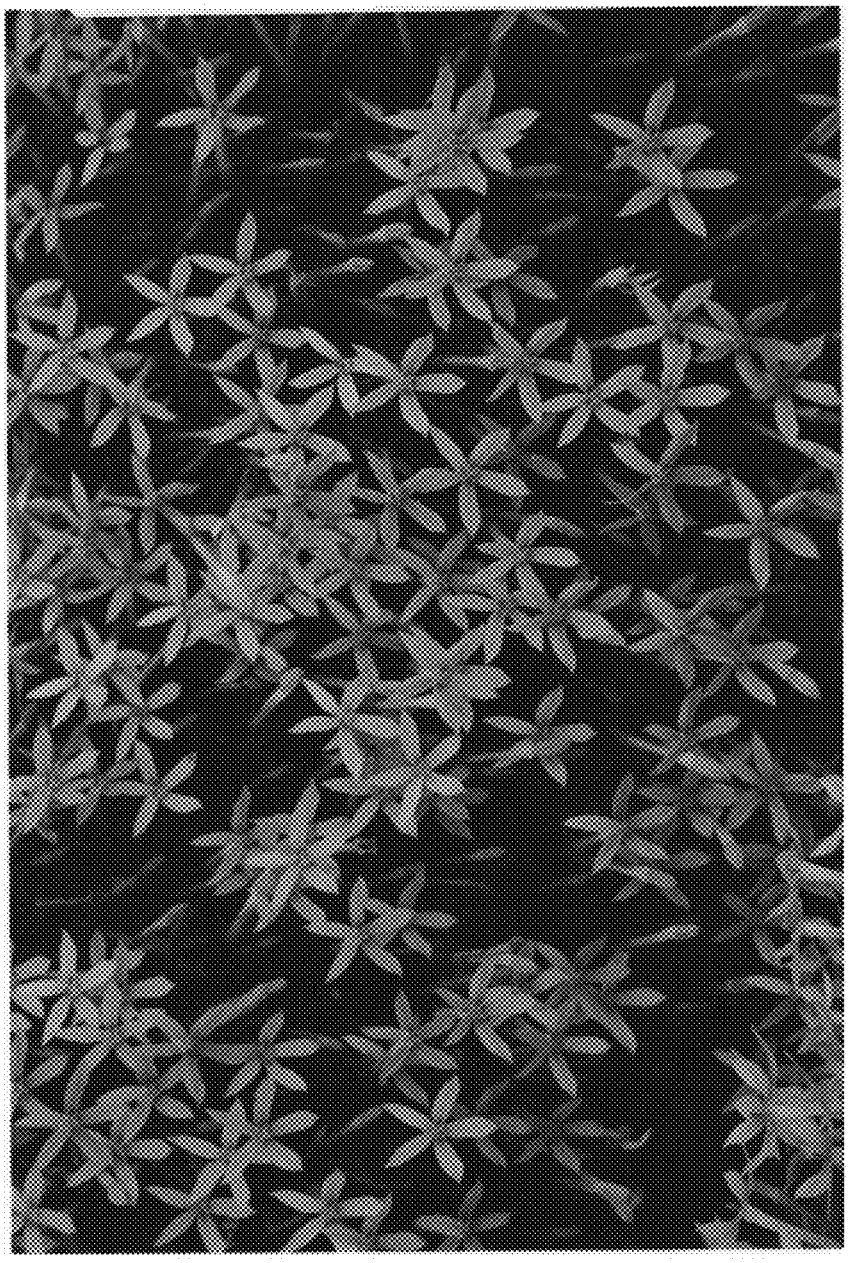

The photograph on the second sheet (FIG. 2 of 2) is a close-up view of a typical flowering plant of 'Isopapi'.

DETAILED BOTANICAL DESCRIPTION

Plants used for the aforementioned photographs and the following observations, measurements and values were grown during the summer and autumn in 19-cm containers in a glass-covered greenhouse in Dresden, Germany and under cultural practices typical of commercial *Isotoma* production. During the production of the plants, day temperatures were at a minimum of 20° C., night temperatures were at a minimum of 16° C. and light levels ranged from 15 kilolux to 100 kilolux. Plants were pinched one time two weeks after planting rooted young plants. Plants were six months old when the description was taken and seven months old when the photographs were taken. In the following description, color references are made to The Royal Horticultural Society Colour Chart, 1995 Edition, except where general terms of ordinary dictionary significance are used.

Botanical classification: *Isotoma axillaris* 'Isopapi'.

Parentage:

*Female, or seed, parent*.—Unnamed proprietary selection of *Isotoma axillaris*, not patented.

*Male, or pollen, parent*.—Unnamed proprietary selection of *Isotoma axillaris*, not patented.

Propagation:

*Type*.—By terminal cuttings.

*Time to initiate roots, summer and winter*.—About 20 days at temperatures about 20° C.

*Time to produce a rooted young plant, summer and winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; moderately dense.

Plant description:

*Plant form and growth habit*.—Herbaceous perennial; broadly upright plant habit; freely branching habit; when pinched, numerous lateral branches develop per plant; moderate vigorous growth habit; moderate growth rate.

*Plant height, soil level to top of foliar plane*.—About 30 cm to 35 cm.

*Plant height, soil level to top of floral plane*.—About 35 cm to 40 cm.

*Plant width* (*spread*).—About 30 cm.

*Lateral branches*.—Length: About 30 cm to 35 cm. Diameter: About 2 mm to 4 mm. Internode length: About 1 cm to 3 cm. Strength: Moderately strong. Texture and luster: Smooth, glabrous; glossy. Color: Close to 144A.

Leaf description:

*Arrangement*.—Alternate, simple; sessile.

*Length*.—About 6 cm.

*Width*.—About 3 cm.

*Shape*.—Lanceolate to oblong.

*Apex*.—Acute.

*Base*.—Oblong.

*Margin*.—Denticulate.

*Texture and luster, upper and lower surfaces*.—Smooth, glabrous; glossy.

*Venation pattern*.—Pinnate.

*Color*.—Developing and fully expanded leaves, upper surface: Close to 138A; venation, close to 138A. Developing and fully expanded leaves, lower surface: Close to 138B; midvein, close to 138C and lateral venation, close to 138B.

Flower description:

*Flower type and flowering habit*.—Single star-shaped flowers; flowers face mostly upright; freely flowering habit with numerous flowers per plant.

*Fragrance*.—None detected.

*Natural flowering season*.—Plants begin flowering about 10 to 15 weeks after planting rooted young plants; in the garden, flowering is continuous from mid-May until frost in Central Europe.

*Flower longevity*.—Flowers last several days on the plant; flowers persistent.

*Flower buds*.—Height: About 3 cm. Diameter: About 5 mm. Shape: Narrowly oblong. Texture and luster: Smooth, glabrous; semi-glossy. Color: Close to 145B to 145D

*Flower diameter*.—About 2.8 cm to 3.2 cm.

*Flower length*.—About 3 cm to 3.5 cm.

*Throat diameter*.—About 4 mm.

*Tube length*.—About 2.5 cm to 3 cm.

*Tube diameter*.—About 4 mm.

*Petals*.—Quantity per flower: Typically five in a single whorl; petals fused at the base into a tubular throat. Length: About 1.5 cm to 2 cm. Width: About 5 mm. Shape: Narrowly oblong. Apex: Acute. Margin: Entire, not undulate. Texture and luster, upper and lower surfaces: Smooth, glabrous; semi-glossy. Color: When opening and fully opened, upper surface: Close to 80A; color does not change with development. When opening and fully opened, lower surface: Close to 155D; color does not change with development. Throat: Close to 80A. Tube: Close to 155D.

*Sepals*.—Quantity per flower: Typically five in a single whorl. Length: About 5 mm to 6 mm. Width: About 1 mm. Shape: Oblong to deltoid. Apex: Acute. Margin: Entire. Texture and luster, upper and lower surfaces: Smooth, glabrous; slightly glossy. Color, upper and lower surfaces: Close to 144A.

*Peduncles*.—Length: About 8 cm to 10 cm. Diameter: About 1 mm. Angle: About 10° to 45° from vertical. Strength: Moderately strong; flexible. Texture and luster: Smooth, glabrous; slightly glossy. Color: Close to 144A.

*Reproductive organs*.—Stamens: Quantity per flower: Typically five. Filament length: About 2 mm to 3 mm. Filament color: Close to 4D. Anther size: About 1 mm by 5 mm. Anther shape: Oblong. Anther color: Close to 4D and 93A. Pollen amount: Abundant. Pollen color: Light yellow. Pistils: Quantity per flower: One. Pistil length: About 2 cm to 3 cm. Stigma shape: Rounded. Stigma color: Close to 76A. Style length: About 2 cm to 3 cm. Style color: Close to 4C. Ovary color: Close to 4C.

*Fruits*.—Length: About 1 cm to 1.2 cm. Diameter: About 5 mm. Color: Close to 164B.

*Seeds*.—Quantity per flower: Numerous. Length: Less than 1 mm. Diameter: Less than 1 mm. Color: Brown.

Pathogen & pest resistance: To date, plants of the new *Isotoma* have not been noted to be resistant to pathogens and pests common to *Isotoma* plants.

Garden performance: Plants of the new *Isotoma* have been observed to have good garden performance and tolerate rain, wind and temperatures ranging from about 1° C. to about 30° C.

It is claimed:

1. A new and distinct *Isotoma* plant named 'Isopapi' as illustrated and described.

* * * * *